United States Patent
Moon et al.

(10) Patent No.: US 8,055,058 B2
(45) Date of Patent: Nov. 8, 2011

(54) APPARATUS AND METHOD FOR DETECTING DEFECTS IN WAFER USING LINE SENSOR CAMERA

(75) Inventors: U-Seock Moon, Gyeonggi-do (KR); Jong-Kyu Han, Gyeonggi-do (KR); Byoung-Moon Hwang, Seoul (KR); Jin-Seob Kim, Gyeonggi-do (KR)

(73) Assignee: Hantech Co., Ltd., Gyeonggi-do (KR)

( * ) Notice: Subject to any disclaimer, the term of this patent is extended or adjusted under 35 U.S.C. 154(b) by 684 days.

(21) Appl. No.: 12/296,134

(22) PCT Filed: Feb. 7, 2007

(86) PCT No.: PCT/KR2007/000673
§ 371 (c)(1), (2), (4) Date: Oct. 6, 2008

(87) PCT Pub. No.: WO2007/091846
PCT Pub. Date: Aug. 16, 2007

(65) Prior Publication Data
US 2009/0257646 A1 Oct. 15, 2009

(30) Foreign Application Priority Data
Feb. 7, 2006 (KR) .................. 10-2006-0011840

(51) Int. Cl.
*G06K 9/00* (2006.01)
(52) U.S. Cl. ............... 382/145; 356/237.5; 250/559.45
(58) Field of Classification Search ............ 382/145
See application file for complete search history.

(56) References Cited

U.S. PATENT DOCUMENTS

| | | | | |
|---|---|---|---|---|
| 4,685,139 A | * | 8/1987 | Masuda et al. | 382/112 |
| 5,153,444 A | * | 10/1992 | Maeda et al. | 250/559.05 |
| 5,528,359 A | * | 6/1996 | Taguchi | 356/237.6 |
| 5,981,949 A | | 11/1999 | Leahy et al. | |
| 6,169,282 B1 | * | 1/2001 | Maeda et al. | 250/310 |
| 2005/0116187 A1 | | 6/2005 | Uda et al. | |

FOREIGN PATENT DOCUMENTS
JP 6-207914 A 7/1994
JP 2004-117150 A 4/2004

OTHER PUBLICATIONS
International Search Report mailed Mar. 30, 2007; PCT/KR2007/000673.

* cited by examiner

*Primary Examiner* — Tarifur Chowdhury
*Assistant Examiner* — Jonathon Cook
(74) *Attorney, Agent, or Firm* — Ladas & Parry LLP

(57) ABSTRACT

An apparatus and method for detecting defects in a wafer are provided. An optical part is disposed under an inspection stage and radiates infrared light. An image obtaining part detects the infrared light transmitted through the wafer to output an image signal. A conveying part conveys the image obtaining part or the inspection stage in a short side direction of a photographing region of a line sensor included in the image obtaining part, and outputs a pulse signal. A controller counts the pulse signal and outputs a photographing instruction signal controlling the image obtaining part to photograph the wafer whenever the wafer is conveyed in the short side direction of the photographing region of the line sensor toward the image obtaining part by a distance corresponding to the length of short sides of the photographing region. A defect detection part combines each image signal to generate an inspection image.

33 Claims, 9 Drawing Sheets

APPARATUS AND METHOD FOR DETECTING DEFECTS IN WAFER USING LINE SENSOR CAMERA

TECHNICAL FIELD

The present invention relates to an apparatus and method for detecting defects in a wafer, and more particularly, to an apparatus and method for detecting positions and sizes of defects existing in a wafer or on its surface.

BACKGROUND ART

In general, a wafer is manufactured through a plurality of subdivided processes, and defects may be generated inside the wafer or on its surface during each process. Such defects may be classified into inherent defects such as cracks in a material itself, and external defects such as foreign substances attached to the wafer surface or contained therein. Defects generated during a process of manufacturing the wafer, depending on their positions and sizes, may result in the wafer having to be discarded. In particular, an air-pocket, a type of molding defect existing in an ingot, may be transferred to a bare wafer manufactured by slicing the ingot. In most cases, a wafer manufactured using a bare wafer having an air-pocket has to be discarded. Therefore, defects should be effectively detected at an appropriate time during the wafer manufacturing process.

One method of inspecting a wafer for defects is a reflective illumination method whereby light is radiated onto a wafer, reflected by the wafer, and detected using a line scan camera or an area camera. However, since this inspection method uses reflected light, a light source that emits with high linearity and intensity should be employed, and the illumination of a work space where the inspection apparatus is installed may have an effect on defect detection results. In addition, since the light source and the camera are disposed on the same space, the inspection apparatus may be quite large.

Another method of inspecting a wafer for defects is a transmissive illumination method whereby infrared radiation is modified according to characteristics of a wafer through which it is transmitted and detected using an infrared camera. An inspection apparatus using a transmissive illumination method is disclosed in U.S. Pat. No. 5,981,949.

Figure 1:
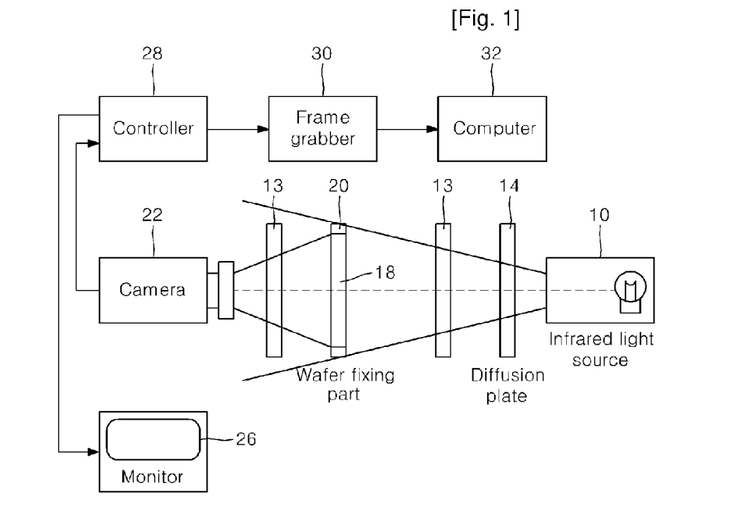
FIG. 1 is a schematic view of a conventional wafer defect inspection apparatus using a transmissive illumination method.

FIG. 1 is a view of a conventional wafer defect inspection apparatus using a transmissive illumination method.

Referring to FIG. 1, the conventional wafer inspection apparatus includes a light source 10, a diffusion plate 14, an optical filter 13, a wafer fixing part 20, an infrared camera 22, a controller 28, a frame grabber 30, a computer 32, and a monitor 26.

The light source 10 is disposed opposite to one surface of the wafer 18 mounted on the wafer fixing part 20 to radiate light onto the wafer 18. The diffusion plate 14 is disposed between the light source 10 and the wafer 18 to uniformly distribute infrared light radiated from the light source 10. The optical filter 13 outputs only infrared wavelengths of the light output from the diffusion plate 14 to the wafer 18, or outputs only infrared wavelengths of the light output from the wafer 18 to the infrared camera 22. The infrared camera 22 is disposed opposite to the other side of the wafer 18 to detect the infrared light transmitted through the wafer 18 and output an image thereof. The controller 28 controls operation of the infrared camera 22, and selectively outputs an image input from the infrared camera 22 to the monitor 26 or the frame grabber 30. The frame grabber 30 digitizes the image input from the controller 28 and outputs the digitized image. The computer 32 analyzes the digitized image input from the frame grabber 30 to determine optical characteristics, defect density, and uniformity of the wafer.

The conventional wafer inspection apparatus having the above constitution can be manufactured to have a simple structure and a compact size, and a single wafer can be inspected within two minutes. However, the time consumed in inspecting a single wafer is much longer than when using an indirect illumination method, thus making it difficult to apply in an actual manufacturing process. In addition, since a plane array infrared camera capable of obtaining an image through a single photographing process and a diffusion plate having an optical transmissivity of 20%-60% are used, in order to obtain an image sufficient to detect defects in a wafer, a high-energy infrared light source should be used.

DISCLOSURE OF INVENTION

Technical Problem

The present invention provides a wafer defect detection apparatus and method capable of rapidly detecting defects in a wafer using a relatively small amount of infrared light.

The present invention also provides a wafer defect detection apparatus and method capable of rapidly detecting defects in a wafer using a relatively small amount of infrared light by minimizing attenuation of input infrared light and uniformly distributing the infrared light.

The present invention also provides a wafer defect detection apparatus and method capable of rapidly detecting defects in a wafer using a relatively small amount of infrared light by readily adjusting uniformity of illumination when luminous intensity output from a light source is reduced as a result of changing the light source or lapse of time.

Technical Solution

According to an aspect of the present invention, an apparatus for detecting defects in a wafer includes: an inspection stage having an inspection region, on which a wafer to be inspected is disposed, formed of a transmissive material; an optical part disposed under the inspection stage and radiating infrared light onto the wafer to be inspected; an image obtaining part formed of a plurality of line sensors having a striped photographing region, and detecting the infrared light transmitted through the wafer disposed on the inspection stage to output an image signal; a conveying part for conveying the image obtaining part or the inspection stage in a short-side direction of the photographing region of the line sensor, and outputting a pulse signal having a predetermined period corresponding to a relative straight moving distance between the image obtaining part and the inspection stage; a controller for counting the pulse signal and controlling the image obtaining part to photograph the wafer whenever the wafer is conveyed in the short-side direction of the photographing region of the line sensor toward the image obtaining part by a distance corresponding to the length of short sides of the photographing region; and a defect detection part for combining each image signal output from the image obtaining part to generate an inspection image corresponding to the wafer, and detecting positions of defects existing in the wafer from the generated inspection image, wherein each of the line sensors transmits charges accumulated therein to a line sensor adjacent in an opposite direction of the conveyance direction when a photographing instruction signal is input from the controller, and then detects the infrared light transmitted through the wafer disposed on the inspection stage, and the line sensor positioned at an end in an opposite direction of the conveyance direction outputs charges accumulated therein as the image signal from a time when the number of input photographing signals exceeds the number of line sensors.

According to another aspect of the present invention, a method of detecting defects in a wafer includes: (a) positioning a wafer to be inspected in an inspection region on an inspection stage, the inspection region being formed of a transmissive material; (b) conveying an image obtaining apparatus having a plurality of line sensors having a striped photographing region, or the inspection stage in a short-side direction of a photographing region of the line sensor, and outputting a pulse signal having a predetermined period corresponding to a relative straight moving distance between the image obtaining apparatus and the inspection stage; (c) counting the pulse signal and outputting a photographing instruction signal to the image obtaining apparatus whenever the wafer is conveyed in the short-side direction of the photographing region of the line sensor toward the image obtaining apparatus by a distance corresponding to the length of short sides of the photographing region; (d) detecting infrared light radiated from a light source disposed under the inspection stage and transmitted through the wafer using the image obtaining apparatus, and outputting an image signal; and (e) combining the image signals to generate an inspection image corresponding to the wafer, and detecting positions of defects existing in the wafer from the generated inspection image, wherein each of the line sensors transmits charges accumulated therein to a line sensor adjacent in an opposite direction of the conveyance direction when a photographing instruction signal is input, and then detects the infrared light transmitted through the wafer disposed on the inspection stage, and the line sensor positioned at an end in an opposite direction of the conveyance direction outputs charges accumulated therein as the image signal from a time when the number of input photographing signals exceeds the number of line sensors.

Advantageous Effects

As a result, it is possible to rapidly and precisely detect defects existing in a wafer using a relatively small amount of infrared light.

BRIEF DESCRIPTION OF THE DRAWINGS

The above and other objects, features and advantages of the present invention will become apparent by describing certain exemplary embodiments thereof with reference to the attached drawings, in which.

MODE FOR THE INVENTION

Hereinafter, an apparatus and method for detecting defects in a wafer in accordance with an exemplary embodiment of the present invention will be described with reference to the accompanying drawings.

Figure 2:
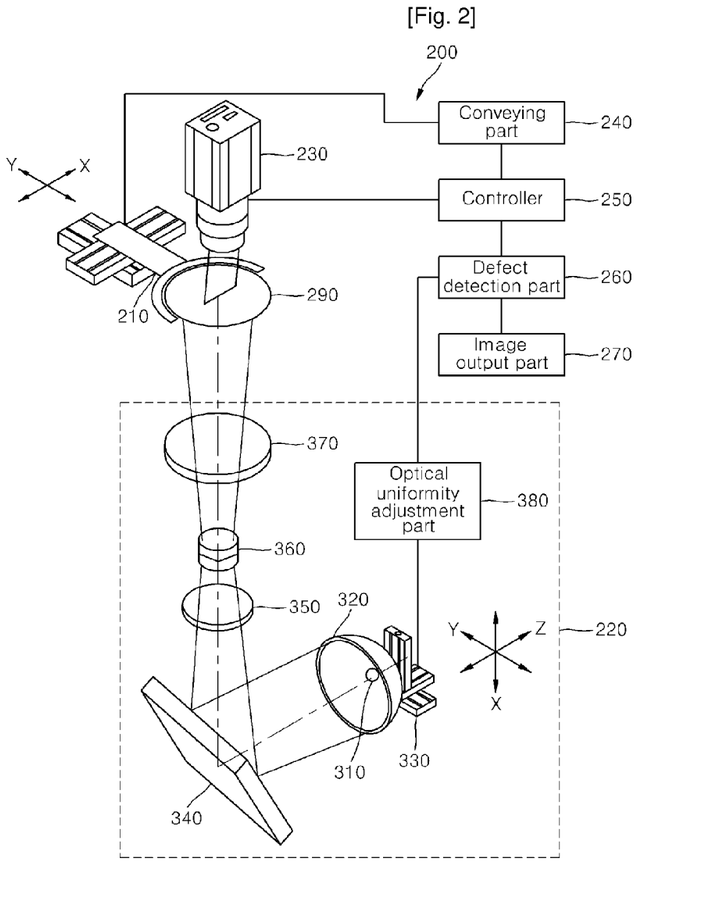
FIG. 2 is an exploded perspective view of an apparatus for detecting defects in a wafer in accordance with an exemplary embodiment of the present invention.

FIG. 2 is an exploded perspective view of an apparatus for detecting defects in a wafer in accordance with an exemplary embodiment of the present invention.

Referring to FIG. 2, an apparatus 200 for detecting defects in a wafer in accordance with the present invention includes an inspection stage 210, an optical part 220, an image obtaining part 230, a conveying part 240, a controller 250, a defect detection part 260, and an image output part 270.

The inspection stage 210 has an inspection region on which a wafer 290 to be inspected is disposed. The inspection region has an area corresponding to the size of the wafer 290, and is formed of a transparent material such as glass. In addition, the inspection stage 21 may have a through-hole having a diameter corresponding to the size of the wafer 290 and acting as the inspection region. At this time, the air in the through-hole acts as a transparent material.

The optical part 220 is disposed under the inspection stage 210 to radiate infrared light onto the wafer 290 to be inspected. The optical part 220 includes an infrared lamp 310, a collecting mirror 320, a positioning stage 330, a reflecting mirror 340, a cold mirror 350, a fly-eye lens 360, a collecting lens 370, and an optical uniformity adjustment part 380.

The infrared lamp 310 emits infrared light having a wavelength of 750-850 nm, and more preferably 790 nm. The infrared lamp 310 may be a halogen lamp. The collecting mirror 320 reflects the infrared light emitted from the infrared lamp 310 to converge the infrared light in one direction. The infrared lamp 310 and the collecting mirror 320 are fixed to the positioning stage 330, and the positioning stage 330 includes x, y and z stages movable in three axial directions constituting an orthogonal coordinate system. Positions of the infrared lamp 310 and the collecting mirror 320 may be changed by movement of the positioning stage 330.

Figure 3:
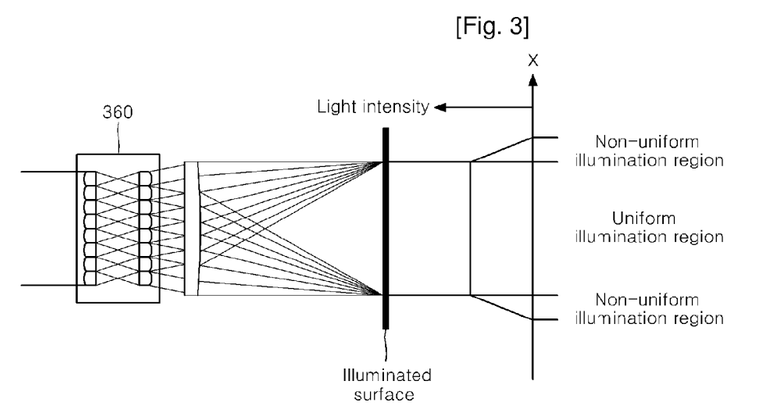
FIG. 3 is a view showing optical distribution of an effective light source formed by a fly-eye lens.

The reflecting mirror 340 changes an optical path of the infrared light emitted from the infrared lamp 310 and the infrared light reflected by the collecting mirror 320. By changing the optical path using the reflecting mirror 340, the apparatus can be minimized. When the infrared lamp 310 is installed opposite to the inspection stage 210, the reflecting mirror 340 may be unnecessary. The cold mirror 350 reflects visible wavelengths of the infrared light output from the infrared lamp 310 and selectively transmits only infrared wavelengths. The fly-eye lens 360 includes a first fly-eye lens comprised of a plurality of fine lens cells having rectangular cross-sections and disposed in a matrix to divide the infrared light emitted from the infrared lamp 310 into fine lens cell units and output the divided light, and a second fly-eye lens comprised of a plurality of fine lens cells having rectangular cross-sections and disposed in a matrix to convert the divided light input from the first fly-eye lens into parallel light and output the parallel light. FIG. 3 is a view showing optical distribution of an effective light source formed by the fly-eye lens 360. The collecting lens 370 concentrates the infrared light transmitted through the fly-eye lens 360 onto the wafer 290. The cold mirror 350 among the above components of the optical part 220 is optional.

The optical uniformity adjustment part 380 improves uniformity of light radiated onto the wafer 290 by driving the positioning stage 330 to change the position of the infrared lamp 310 when a deviation between grey scale values (brightness of an image ranging from 0 to 255) of a plurality of partial images detected from an inspection image generated from a sample wafer having no defect exceeds a predetermined reference value. Each of the partial images is formed of a single pixel or a plurality of pixels. When the partial image is formed of a plurality of pixels, an average value or an intermediate value of grey scale values of the pixels constituting the partial image is set as a grey scale value of the partial image. Meanwhile, the deviation between the grey scale values of the partial images may be taken as the difference between the highest and the lowest of the grey scale values, the largest difference between the average of the grey scale values of the partial images and grey scale values of the respective partial images, or may be calculated by some other method. In addition, the reference value may be set depending on a method of calculating a deviation between the respective grey scale values of the partial images in different manners. When the deviation between the respective grey scale values of the partial images uses the difference between the average of the grey scale values of the partial images and the respective grey scale values of the partial images, the reference value may be set such that the difference is within 5% of the average value.

Figure 4:
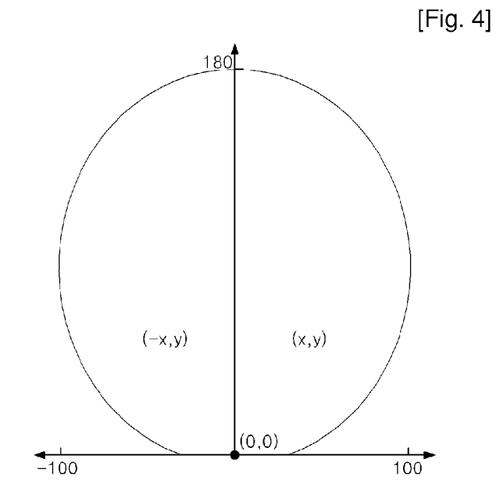
FIG. 4 is a diagram showing positions and coordinates of partial images on a coordinate system set on an inspection image of a sample wafer.

For example, when grey scale values of four partial images detected from an inspection image of a sample wafer are 100, 100, 120 and 90, the difference between the highest and the lowest of the grey scale values is 30. Here, when the reference value is set as 10, since the difference between the highest and the lowest of the grey scale values exceeds the reference value, the optical uniformity adjustment part 380 drives the positioning stage 330 to change the position of the infrared lamp 310. In this case, movement of the positioning stage 330 by the optical uniformity adjustment part 380 is determined by coordinates of the partial images. That is, as shown in FIG. 4, when coordinates and grey scale values of the partial images on a coordinate system set to the inspection image of the sample wafer are as listed in Table 1, the optical uniformity adjustment part 380 moves the positioning stage 330 by a distance corresponding to the difference between the highest and the lowest of the grey scale values in a positive y-axis direction (or a positive y-axis direction and a positive z-axis direction). Here, x- and y-axes of the positioning stage 330 are set to correspond to x- and y-axes on the coordinate system set to the inspection image of the sample wafer, and a positive z-axis direction is set to correspond to a direction in which the positioning stage 330 moves toward the reflecting mirror 340.

TABLE 1

|  | Partial Image 1 | Partial Image 2 | Partial Image 3 | Partial Image 4 |
|---|---|---|---|---|
| Coordinates | (50,0) | (−50,0) | (0,40) | (0,140) |
| Grey scale Values | 100 | 100 | 120 | 90 |

Meanwhile, an operator may manually improve optical uniformity using the positioning stage 330. In this case, the operator functions as the optical uniformity adjustment part 380. The operator changes the position of the positioning stage 330 on the basis of a brightness difference recognized from the inspection image generated from the sample wafer having no defect output through the image output part 280, thereby improving optical uniformity. Although the operator manually operates the positioning stage 330, the optical uniformity adjustment part 380 may be employed. The optical uniformity adjustment part 380 outputs a deviation between the respective grey scale values of the partial images detected from the inspection image, or movement to each axis of the positioning stage 330 calculated on the basis of the deviation between the grey scale values, to the image output part 280. In this case, the operator changes the position of the positioning stage 330 on the basis of information output through the image output part 280 to improve optical uniformity.

Figure 5:
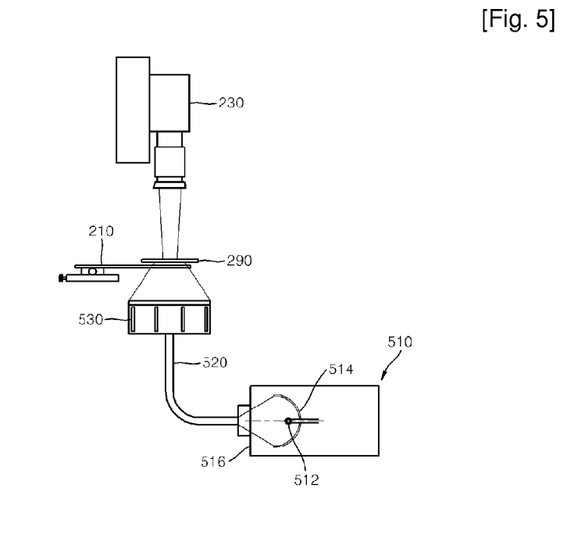
FIGS. 5 and 6 are perspective views of examples of an optical part employing a linear light guide.
Figure 6:
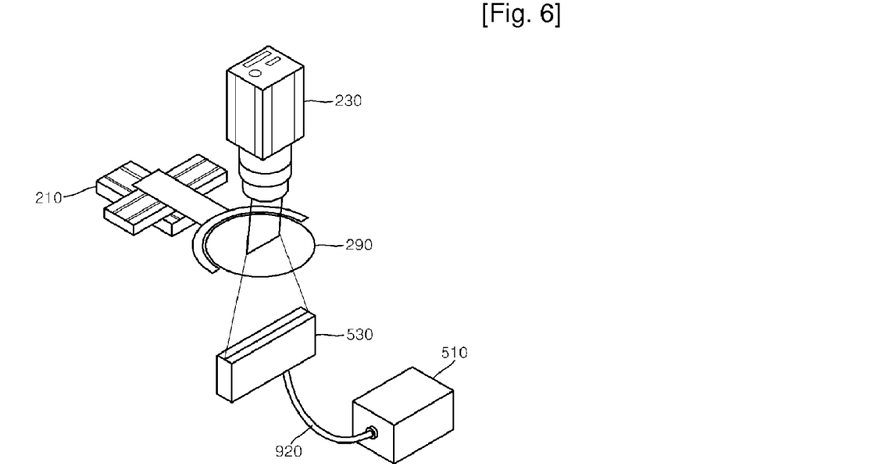

Meanwhile, the optical part 220 may be implemented using a linear light guide. FIGS. 5 and 6 show an example of the optical part 220 employing a linear light guide.

Referring to FIGS. 5 and 6, the optical part 220 includes a light source 510, an optical transmission path 530, and a linear light guide 530. The light source 510 includes an infrared lamp 512, a reflecting mirror 514, and a housing 516. The infrared lamp 512 emits infrared light having a wavelength of 750-850 nm, and more preferably 790 nm. A reflecting mirror 514 is installed at the rear end of the infrared lamp 512 to collect light emitted from the infrared lamp 512 into one side of the housing 516. The infrared lamp 512 may be a halogen lamp. The housing 516 has a space for accommodating the infrared lamp 512. The optical transmission path 520 is fixedly inserted into one side of the housing 516. The optical transmission path 520 fixed to the housing 516 is formed of an optical fiber coated with an optical blocking coating material or an optical waveguide. The linear light guide 530 converts the infrared light transmitted through the optical transmission path 520 into a line of light and outputs the line of light. By employing the linear light guide 530, there is no need to perform optical alignment when changing the infrared lamp 512. In addition, since light is transmitted through the optical fiber or optical waveguide, there is no need to dispose lenses on an optical path, thereby reducing overall manufacturing cost. Further, since the optical uniformity of the infrared light converted into the line of light through the optical fiber or the optical waveguide of the linear light guide 530 is within the ±8% minimum uniformity required to inspect the wafer, performance reduction of the optical part is small compared to the optical part shown in FIG. 2.

The image obtaining part 230 includes a plurality of line sensors having a striped photographing region, and detects infrared light transmitted through the wafer 290 disposed on the inspection stage 330 to output an obtained image signal.

Figure 7:
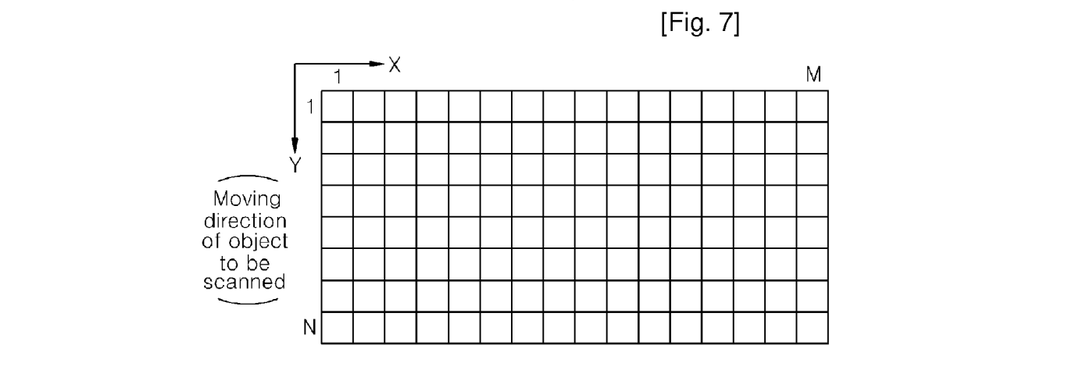
FIG. 7 is a diagram showing positions of a plurality of line sensors installed in an image obtaining part.

The image obtaining part 230 is installed at a position spaced apart from the wafer 290 by a predetermined distance, and a plurality of line sensors are disposed in parallel with each other. Each of the line sensors is formed of 8000 pixels and obtains an image with a resolution of 6 micrometers. Therefore, a photographing region of each line sensor has a long side of 48 mm. In order to obtain the entire image of a wafer having a diameter of 200 mm, at least five scans are required. FIG. 7 is a diagram showing positions of a plurality of line sensors installed in an image obtaining part 230.

The conveying part 240 conveys the image obtaining part 230 or the inspection stage 210 in a short-side direction of the photographing region of the line sensor, and outputs a pulse signal having a predetermined period corresponding to a relative straight moving distance between the image obtaining part 230 and the inspection stage 210. A conveyance speed of the conveying part 240 is varied depending on light intensity. When the intensity of the infrared light radiated onto the wafer 290 is 50 mW, the conveyance speed may be set as 40 mm/sec.

The controller 250 counts the pulse signal input from the conveying part 240, and outputs a photographing instruction signal for controlling to photograph the wafer 290 using the image obtaining part 230 whenever the wafer 290 is conveyed in a short-side direction of the photographing region of the line sensor toward the image obtaining part 230 by a distance corresponding to the length of the short side of the photographing region. A signal having a certain period such as an encoder pulse may be used as a trigger signal for synchronizing a conveyance time of the wafer 290 or the image obtaining part 230 with an output time of the photographing instruction signal. Using the encoder pulse, it is possible to maintain a region of a single line scanned by the line sensor at predetermined intervals. The pulse signal input from the conveying part 240 to the controller 250 corresponds to a trigger signal.

Meanwhile, the photographing instruction signal may be generated by a frame grabber. In this case, the frame grabber counts a trigger signal input from the conveying part 240 and generates a photographing synchronization signal in a pulse form to output the synchronization signal when the number of trigger signals corresponds to the wafer 290 conveyed by a distance corresponding to the length of the short side of the photographing region of the line sensor. The photographing synchronization signal generated by the frame grabber is input to the image obtaining part 230 as a photographing instruction signal. The frame grabber may be implemented as one component of the controller 250, or disposed between the conveying part 240 and the controller 250 as a separate component from the controller 250.

Figure 8:
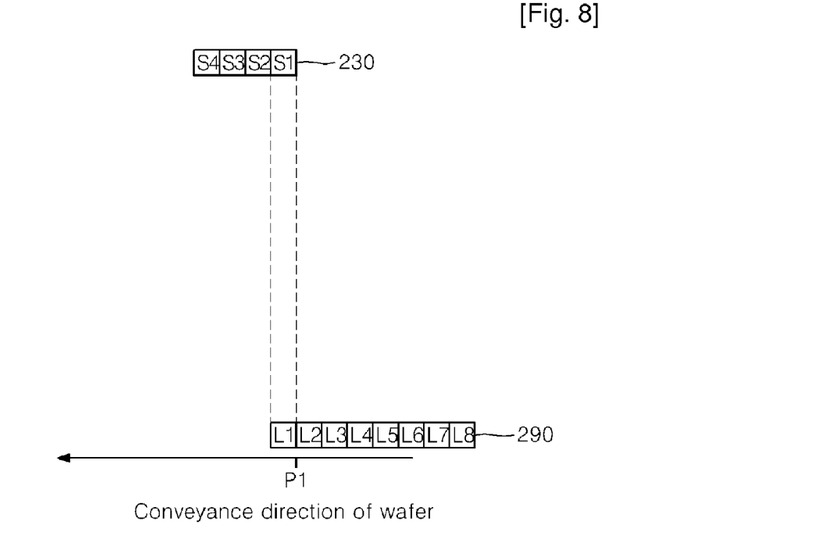
FIG. 8 is a diagram showing an image obtaining process in an image obtaining part depending on movement of a wafer to be inspected.

FIG. 8 is a diagram showing an image obtaining process of the image obtaining part 230 depending on movement of the wafer 290 to be inspected.

Referring to FIG. 8, the image obtaining part 230 is comprised of four line sensors S1 to S4, and photographing regions L1 to L8 corresponding to the line sensors are formed on the wafer 290 to be inspected. As shown in FIG. 7, when the wafer 290 is conveyed to a scan start position P1, the first line sensor S1 photographs the first photographing region L1 on the wafer 290. Next, when the wafer 290 is conveyed by the length of a short side of the first photographing region L1, the first line sensor S1 transmits charges accumulated therein (i.e., charges accumulated by infrared light detected from the first photographing region L1) to the second line sensor S2 and then photographs the second photographing region L2. In addition, the second line sensor S2 accumulates the charges accumulated by the infrared light detected from the first photographing region L1 and the charges transmitted from the first line sensor S1. Each of the line sensors S1 to S4 repeatedly performs transmission and accumulation of the charges accumulated according to the photographing instruction signal until photographing of the entire wafer 290 is completed in the manner described above. Meanwhile, the fourth line sensor S4 outputs the charges accumulated therein as an image signal of the wafer 290 from the time when the photographing instruction signal is input after exceeding the number of line sensors S1 to S4 (i.e., when a fifth photographing instruction signal is input). An image signal output from the fourth line sensor S4 (i.e., an output signal of the image obtaining part 230) may be input to the defect detection part 260 directly or after storing in storage means (not shown).

While the image obtaining process described with reference to FIG. 8 is performed by a line sensor camera including a plurality of line sensors employed as the image obtaining part 230, even when a time delay and integration (TDI) line scan camera is employed as the image obtaining part 230, the image may be obtained in the same manner as described above. At this time, the TDI line scan camera including several tens of line sensors can transmit charges accumulated in each line sensor to adjacent line sensors as the line sensors move relative to an object to obtain a charge accumulation effect corresponding to the number of line sensors, so that the TDI line scan camera can obtain an image of approximately one hundred times higher sensitivity than a general line scan camera under the same conditions. When the TDI line scan camera is used, even though low-intensity infrared light is radiated, it is possible to rapidly detect the light transmitted through the wafer.

Figure 9:
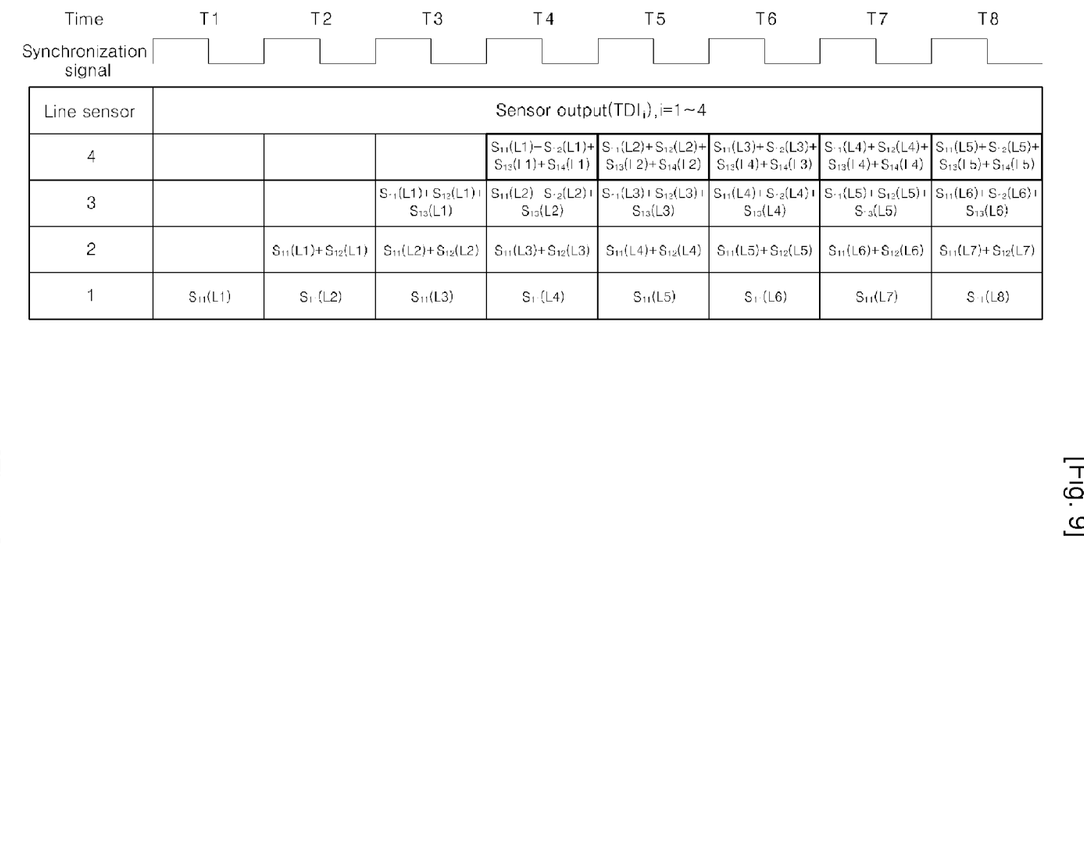
FIG. 9 is a diagram of signals output from line sensors depending on photographing instruction signals.

FIG. 9 is a diagram of signals output from line sensors depending on photographing instruction signals.

Referring to FIG. 9, each of the line sensors S1 to S4 detects infrared light input from the corresponding photographing region on the wafer 290 to accumulate charges whenever a synchronization signal (i.e., a photographing instruction signal) is input. Here, the fourth line sensors S4 outputs the accumulated charges to the defect detection part 260 when an eighth (a multiple of four) synchronization signal is input. An output signal of the line sensor of FIG. 7 is represented as $S_{ij}(L_k)$. Here, i ranges from 1 to 1 (1 is the number of line sensors), k is the number of photographing regions on the wafer, and j ranges from 1 to [k/l]+1 ([x] is the largest integer not greater than x). Therefore, when l=4 and k=25, j=7.

The defect detection part 260 combines image signals input from the image obtaining part 230 to generate an inspection image corresponding to the wafer 290, and detects positions and sizes of defects (i.e., particles or air-pockets) existing in the wafer 290 from the generated inspection image. Here, the defect detection part 260 can detect whether the wafer 290 is good or bad on the basis of the number of defects detected, as well as the positions and sizes of the defects existing in the wafer 290. A reference value for determining whether the wafer 290 is good or bad is pre-set.

Figure 10:
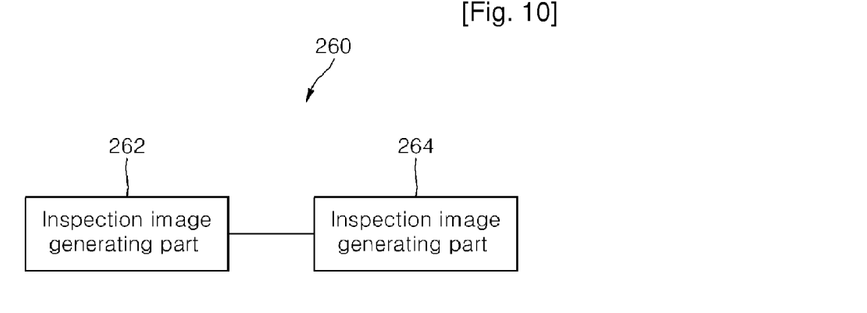
FIG. 10 is a block diagram of a defect detection part.

FIG. 10 is a block diagram of the defect detection part 260.

Referring to FIG. 10, the defect detection part 260 includes an inspection image generating part 262 and a defect determination part 264. The inspection image generating part 262 combines image signals input from the image obtaining part 230 to generate an inspection image corresponding to the wafer 290. The defect determination part 264 determines the region in which the absolute value of the difference between a grey scale value of pixels constituting an inspection image generated by the inspection image generating part 262 and a pre-set reference grey scale value is larger than a predetermined reference value (for example, ±30 with reference to a grey scale value of a reference image obtained from a wafer having no defect), as a defect region. The grey scale value is in the range of 0-255 depending on brightness. Here, the positions of the defects are represented as coordinates on a coordinate system set with respect to an inspection image of the sample wafer as shown in FIG. 6. Further, the apparatus may be configured to allow the defect determination part 264 to detect a defect in the wafer 290 only when there is a defect region having a diameter larger than a predetermined diameter (e.g., 30□), among the determined defect regions.

Figure 11:
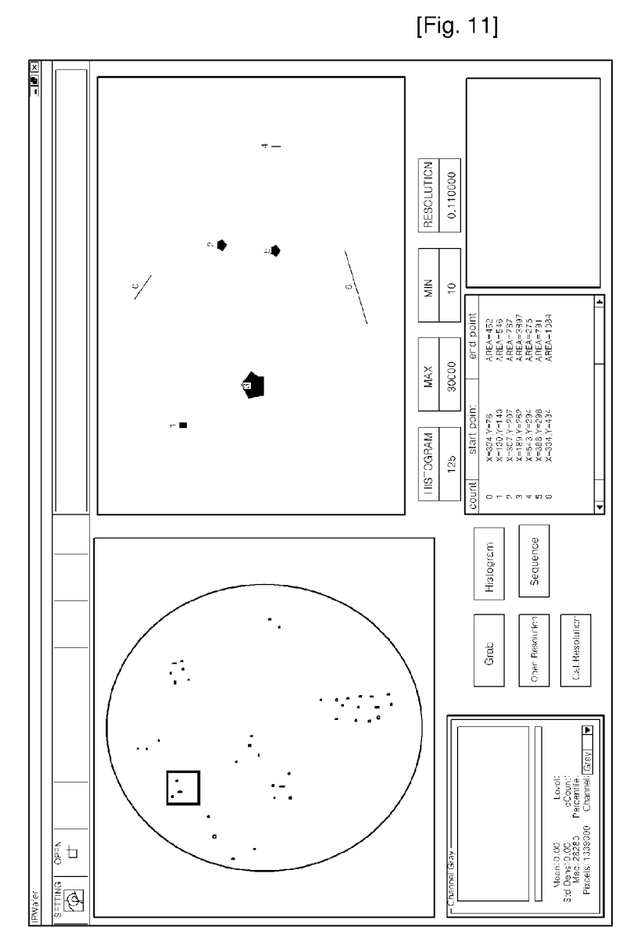
FIGS. 11 and 12 are views of an example of a user interface screen of an inspection image output to an image output part, and an enlarged image of an air-pocket detected from a wafer, respectively.
Figure 12:
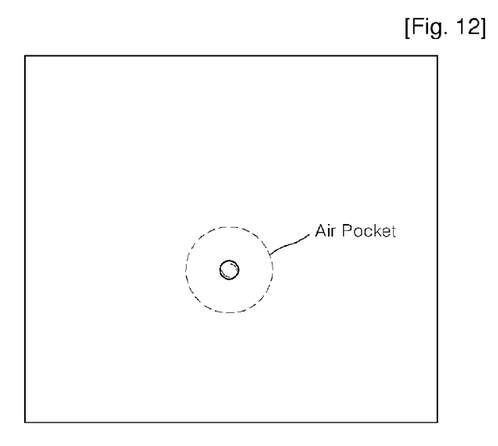

The image output part 270 outputs an inspection image, position and size information of the defects, and an enlarged image of the defect, which are generated by the defect detection part 260. In addition, the image output part 270 outputs information on a current state of the wafer defect detection apparatus 200, a user interface screen, and so on. Therefore, an operator can control processes of driving the apparatus and inspecting defects on the basis of information output through the image output part 270. FIGS. 11 and 12 are views of an example of a user interface screen of an inspection image output to the image output part 270, and an enlarged image of an air-pocket detected in the wafer, respectively.

Figure 13:
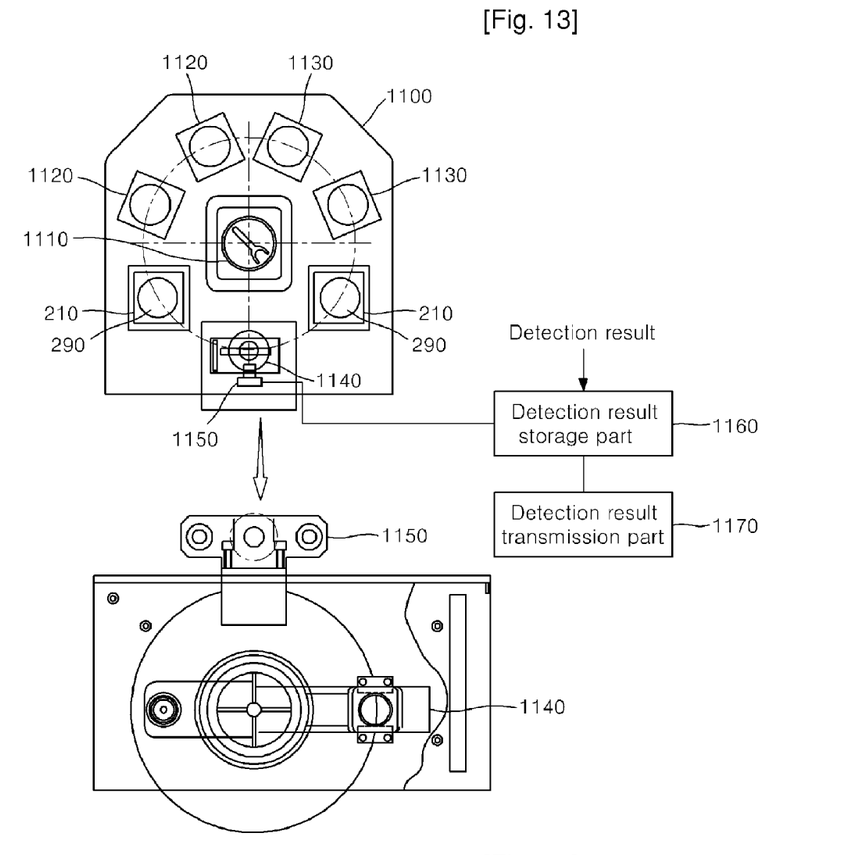
FIG. 13 is a plan view of an apparatus for detecting defects in a wafer in accordance with another exemplary embodiment of the present invention.

FIG. 13 is a plan view of an apparatus for detecting defects in a wafer in accordance with another exemplary embodiment of the present invention.

Referring to FIG. 13, an apparatus 1100 for detecting defects in a wafer in accordance with the present invention includes a wafer conveying part 1110, a first cassette 1120, a second cassette 1130, an alignment part 1140, an optical character reading part 1150, a detection result storage part 1160, and a detection result transmission part 1170, in addition to the components of the wafer defect detection apparatus 200 described with reference to FIG. 2. Detailed description of the components of the wafer defect detection apparatus 200 already described with reference to FIG. 2 will not be repeated and those components will be designated by the same reference numerals as in FIG. 2.

The wafer conveying part 1110 extracts a wafer 290 to be inspected from a supply cassette in which wafers are mounted, conveys the wafer 290 onto an inspection region on an inspection stage 210, and removes the wafer 290 from the inspection region after completion of defect inspection of the wafer 290 by a defect detection part 260. The first cassette 1120 accommodates wafers 290 determined to have defects and the second cassette 1130 accommodates wafers 290 determined to have no defects. Each of the first cassette 1120 and the second cassette 1130 may be comprised of a plurality of cassettes. In addition, the wafer 290 removed from the inspection region after the inspection is conveyed to and accommodated in the first cassette 1120 or the second cassette 1130 using the wafer conveying part 110.

The alignment part 1140 recognizes a flat zone formed at the wafer 290 and aligns the wafer 290 thereto. Here, the wafer conveying part 1110 conveys the wafer 290 to the alignment part 1140, aligns the wafer 290, and then conveys the wafer 290 onto the inspection range on the inspection stage 210.

Figure 14:
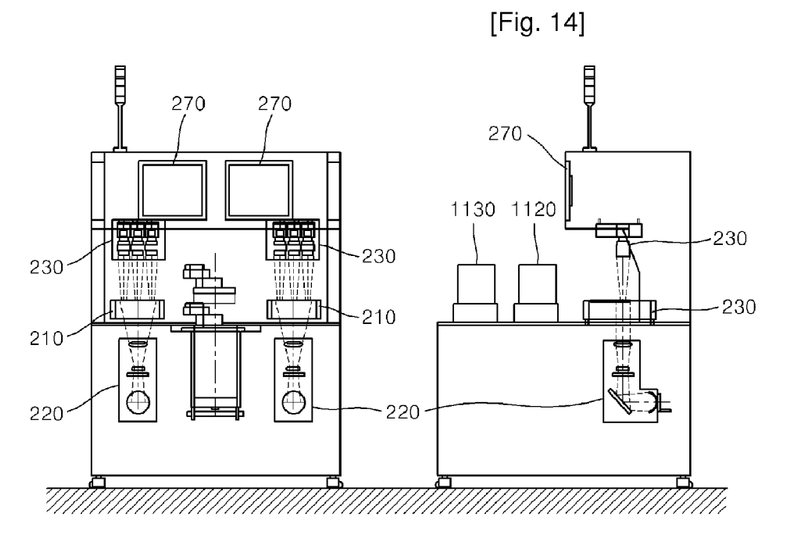
FIG. 14 is a schematic cross-sectional view of the apparatus for detecting defects in a wafer shown in FIG. 13.

The optical character reading part 1150 reads inherent identification information given to the wafer 290. The detection result storage part 1160 stores the defect detection result detected by the defect detection part 260 on the basis of the identification information read from the wafer using the optical character reading part 1150. The detection result transmission part 1170 transmits the defect detection result stored in the detection result storage part 1160 or the defect detection result input from the defect detection part 260 to an inspection management sever (not shown) connected to the detection result transmission part 1170 through a wired or wireless communication network. Here, the wafer 290 whose defect detection has been completed may not be accommodated in one of the first cassette 1120 and the second cassette 1130 according to the defect detection result, but rather the defect detection result alone may be transmitted to the inspection management server. Meanwhile, the alignment part 1140, the optical character reading part 1150, the detection result storage part 1160, and the detection result transmission part 1170 are optionally installed. Also, the alignment part 1140 and the optical character reading part 1150 may be integrated as a single component. FIG. 14 is a schematic cross-sectional view of the apparatus for detecting defects in a wafer shown in FIG. 13.

Figure 15:
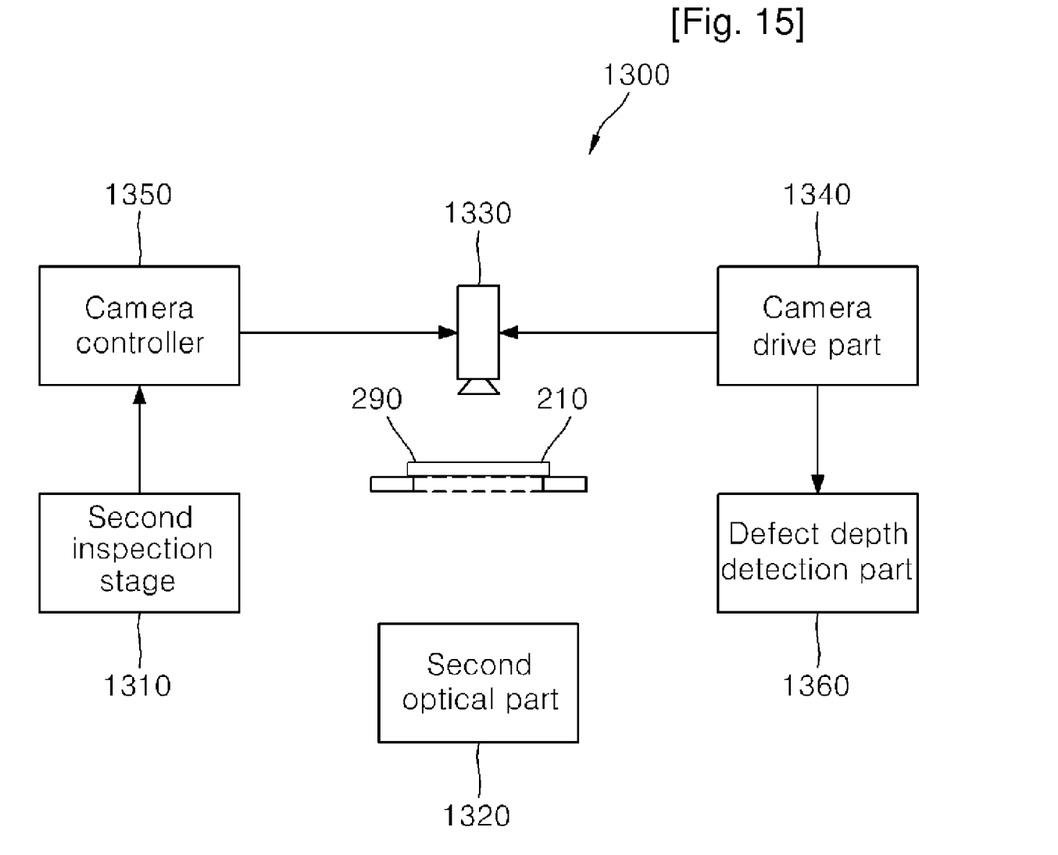
FIG. 15 is a schematic view of an apparatus for detecting defects in a wafer in accordance with still another exemplary embodiment of the present invention.

FIG. 15 is a schematic view of an apparatus for detecting defects in a wafer in accordance with still another exemplary embodiment of the present invention.

Referring to FIG. 15, an apparatus 1300 for detecting defects in a wafer in accordance with the present invention includes a second inspection stage 1310, a second optical part 1320, an area camera 1330, a camera drive part 1340, a camera controller 1350, and a defect depth detection part 1360. The wafer defect detection apparatus 1300 shown in FIG. 13 may be integrated with the wafer defect detection apparatus 200 or 1100 shown in FIG. 2 or 11 as a single apparatus.

The second inspection stage 1310 provides an inspection region for disposing a wafer, defect positions of which are determined by the defect detection part 260, and the inspection region is formed of a transmissive material. The second optical part 1320 is disposed under the second inspection stage 1310 to radiate infrared light onto the wafer disposed on the second inspection stage 1310. Here, the light source of the optical part 220 shown in FIG. 2 may be used as a light source of the second optical part 1320. In this case, the second optical part 1320 may be comprised of a beam splitter disposed on an optical path of the optical part 220 to diverge light, and a reflecting mirror for changing the optical path of the light diverged by the beam splitter to radiate the light onto the inspection region of the second inspection stage 1310. In addition, the optical part shown in FIGS. 5 and 6 may also be used as the light source of the second optical part 1320. In this case, an optical splitter is installed at an intermediate part of the optical transmission path 520 to split light emitted from a light source 510 into the second optical part 1320.

The area camera 1330 detects infrared light transmitted through the wafer disposed on the second inspection stage 1310 to output an obtained image signal. The camera drive part 1340 moves the area camera 1330 such that a focus of the area camera 1330 is formed at the position of the defect on the wafer disposed on the second inspection stage 1310, is driven from one surface of the wafer disposed on the second inspection stage 1310 to the other surface thereof in a direction perpendicular to the surface of the wafer, and outputs a pulse signal having a predetermined period corresponding to a straight moving distance of the area camera 1330. Here, when the wafer has a thickness of 700□, a vertical moving distance of the area camera 1330 is also 700□. The camera controller 1350 counts the pulse signal input from the camera drive part 1340, and outputs a photographing instruction signal for controlling the area camera 1330 to photograph the wafer disposed on the second inspection stage 1310 whenever a pre-set number of pulse signals is input. The defect depth detection part 1360 detects the depth of the defect in the wafer disposed on the second inspection stage 1310 on the basis of the counted number of accumulated pulse signals at the time when a photographing instruction signal corresponding to an image signal having the clearest defect region among the image signals photographed by the area camera 1330 according to the photographing instruction signal input from the camera controller 1350 is output. In the case that the camera drive part 1340 is set to output a pulse whenever the area camera 1330 moves by 0.1 nm in a direction from a lower surface of the wafer to an upper surface thereof, when the counted number of pulse signals accumulated at the time of the output of the photographing instruction signal corresponding to the image signal having the clearest defect region is 100, the depth of the defect is 10 nm from the lower surface of the wafer.

Figure 16:
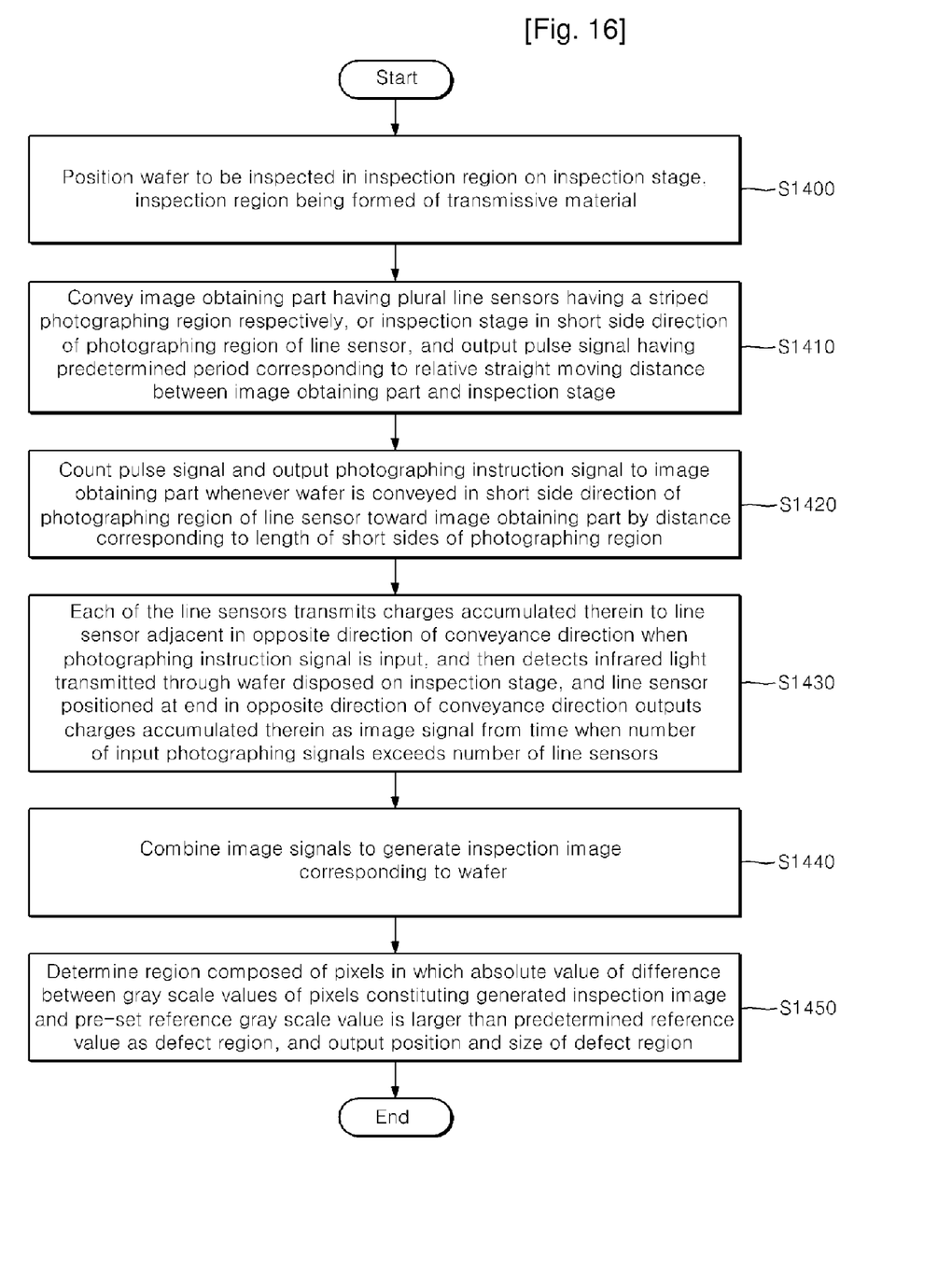
FIG. 16 is a flowchart showing a method of detecting defects in a wafer in accordance with an exemplary embodiment of the present invention.

FIG. 16 is a flowchart showing a method of detecting defects in a wafer in accordance with an exemplary embodiment of the present invention.

Referring to FIG. 16, a wafer 290 to be inspected is disposed in an inspection region formed of a transmissive material on an inspection stage 210 (S1400). Then, a conveyer part 240 conveys an image obtaining part 230 including a plurality of line sensors having striped photographing regions or an inspection stage 210 in a short-side direction of the photographing region of the line sensor, and outputs a pulse signal having a predetermined period corresponding to a relative straight moving distance between the image obtaining part 230 and the inspection stage 210 (S1410). A controller 250 counts the pulse signal and outputs a photographing instruction signal to the image obtaining part 230 whenever the wafer 290 is conveyed toward the image obtaining part 230 by a distance corresponding to the length of a short side of the photographing region in a short-side direction of the photographing region of the line sensor (S1420). Each of the line sensors installed at the image obtaining part 230 transmits charges accumulated therein to the line sensor adjacent in the opposite direction of the conveyance direction when the photographing instruction signal is input, and then detects infrared light transmitted through the wafer 290 disposed on the inspection stage 210. And, the line sensor disposed at an end in an opposite direction of the conveyance direction outputs the charges accumulated therein as an image signal from the time when the number of input photographing instruction signals exceeds the number of line sensors (S1430). A defect detection part 260 combines the image signals to generate an inspection image corresponding to the wafer 290 (S1440). Next, the defect detection part 260 determines the region in which an absolute value of the difference between a grey scale value of pixels constituting the generated inspection image and a pre-set reference grey scale value is larger than a predetermined reference value, as a defect region, and outputs positions and sizes of the defect region (S1450).

Figure 17:
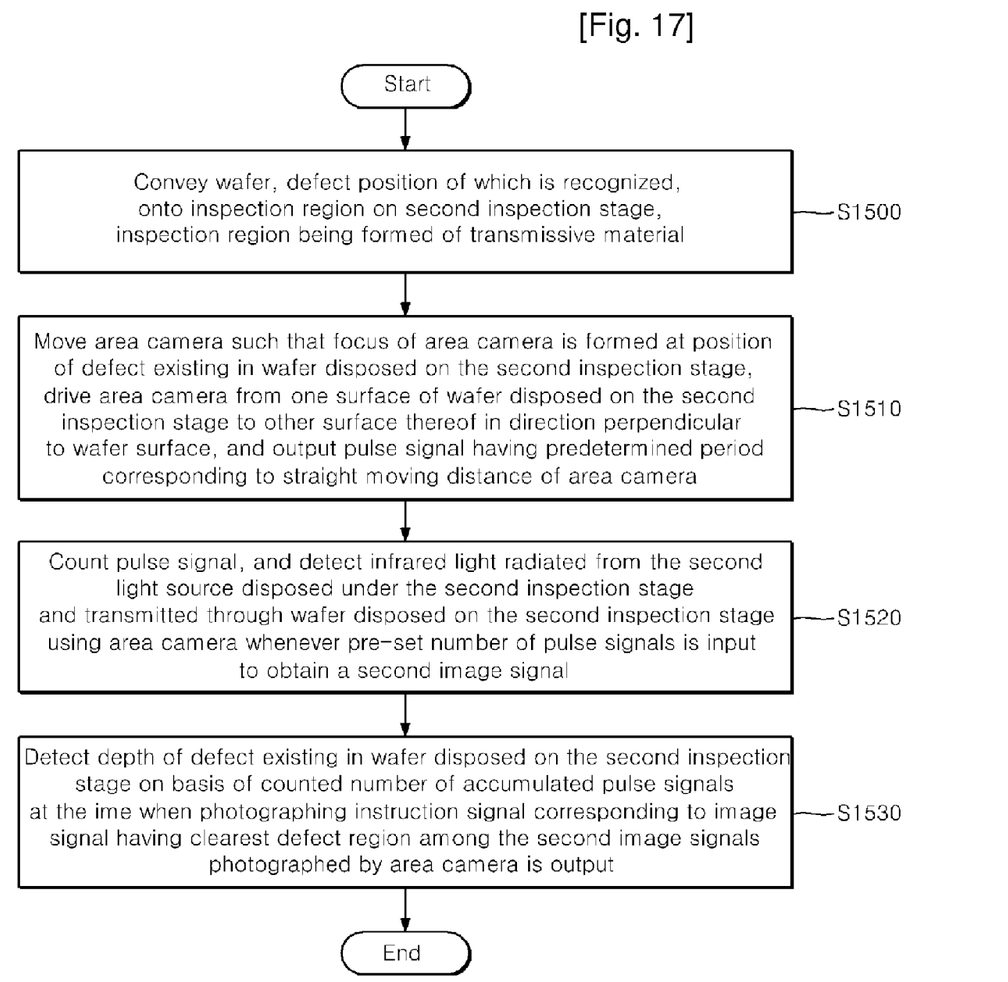
FIG. 17 is a flowchart showing a method of detecting defects in a wafer in accordance with another exemplary embodiment of the present invention.

FIG. 17 is a flowchart showing a method of detecting defects in a wafer in accordance with another exemplary embodiment of the present invention. The method of detecting defects in a wafer shown in FIG. 17 may be performed sequentially after the method of detecting defects in a wafer described with reference to FIG. 14 on the basis of the results of the method of FIG. 16.

Referring to FIG. 17, a wafer, defect positions of which are determined, is conveyed onto an inspection region formed of a transmissive material on the second inspection stage 1310 (S1500). A camera drive part 1340 moves an area camera 1330 such that a focus of the area camera 1330 is formed at the position of the defect in the wafer disposed on the second inspection stage 1310, is driven from one surface of the wafer disposed on the lower inspection stage 1310 to the other surface thereof in a direction perpendicular to the surface of the wafer, and outputs a pulse signal having a predetermined period corresponding to a straight moving distance of the area camera 1330 (S1510). A camera controller 1350 counts a pulse signal, detects infrared light radiated from a second optical part 1320 disposed under the second inspection stage 1310 and transmitted through the wafer disposed on the second inspection stage 1310 using the area camera 1330 whenever a pre-set number of pulse signals in input, and then obtains an image signal (S1520). A defect depth detection part 1360 detects the depth of a defect in the wafer disposed on the second inspection stage 1310 on the basis of the counted number of pulse signals accumulated at the time when a photographing instruction signal corresponding to an image signal having the clearest defect region among the image signals photographed by the area camera 1330 is output (S1530).

An apparatus and method for detecting defects in a wafer in accordance with the present invention is capable of scanning infrared light transmitted through a wafer using line sensors, and accumulating signals obtained by the line sensors to rapidly detect defects from a generated inspection image, thereby ensuring operational compatibility with other apparatuses used in a wafer manufacturing process and enabling practical use of the apparatus. In addition, since infrared light intensity can be minimized by enhancing the uniformity of the light using a fly-eye lens, it is possible to employ a low-power infrared light source. Further, a light source mounting part can be movably installed to readily adjust light uniformity when light intensity is reduced as a result of changing the light source or lapse of time.

The present invention may also be implemented as a computer code stored in a computer-readable recording medium. The computer-readable recording medium includes all kinds of recording devices in which computer data is stored, for example, a read only memory (ROM), a random access memory (RAM), a compact disc read only memory (CD ROM), a magnetic tape, a floppy disc, an optical data storage device, and carrier waves (for example, transmission through the Internet). Further, the computer-readable recording medium may be distributed among computer systems connected via a network such that the computer code can be stored and executed in a decentralized manner.

Although the present invention has been described with reference to certain exemplary embodiments thereof, it will be understood by those skilled in the art that a variety of modifications may be made to the described embodiments without departing from the spirit or scope of the present invention defined by the appended claims, and their equivalents.

The invention claimed is:

1. An apparatus for detecting defects in a wafer, comprising:

an inspection stage having an inspection region, on which a wafer to be inspected is disposed, formed of a transmissive material;

an optical part disposed under the inspection stage and radiating infrared light onto the wafer to be inspected;

an image obtaining part formed of a plurality of line sensors having a striped photographing region respectively, and detecting the infrared light transmitted through the wafer disposed on the inspection stage to output an image signal;

a conveying part for conveying the image obtaining part or the inspection stage in a short-side direction of the photographing region of the line sensor, and outputting a pulse signal having a predetermined period corresponding to a relative straight moving distance between the image obtaining part and the inspection stage;

a controller for counting the pulse signal and controlling the image obtaining part to photograph the wafer whenever the wafer is conveyed in the short-side direction of the photographing region of the line sensor toward the image obtaining part by a distance corresponding to the length of short sides of the photographing region; and a defect detection part for combining each image signal output from the image obtaining part to generate an inspection image corresponding to the wafer, and detecting positions of defects existing in the wafer from the inspection image, wherein each of the line sensors transmits charges accumulated therein to a line sensor adjacent in an opposite direction of the conveyance direction when a photographing instruction signal is input from the controller, and then detects the infrared light transmitted through the wafer disposed on the inspection stage, and the line sensor positioned at an end in an opposite direction of the conveyance direction outputs charges accumulated therein as the image signal from a time when the number of input photographing signals exceeds the number of line sensors.

2. The apparatus for detecting defects in a wafer according to claim 1, wherein the optical part comprises:
   an infrared lamp for emitting the infrared light; and
   a positioning stage having the infrared lamp mounted therein and movable in three axial directions constituting an orthogonal coordinate system.

3. The apparatus for detecting defects in a wafer according to claim 2, wherein the optical part further comprises an optical uniformity adjustment part for detecting a plurality of partial images for adjusting optical uniformity from an inspection image of a sample wafer having no defect, and driving the positioning stage to change a position of the infrared lamp when a difference between the highest and the lowest of gray scale values measured from the partial images is larger than a predetermined reference value.

4. The apparatus for detecting defects in a wafer according to claim 2, wherein the optical part further comprises an optical uniformity adjustment part for detecting a plurality of partial images for adjusting optical uniformity from an inspection image of a sample wafer having no defect, and driving the positioning stage to change a position of the infrared lamp when the highest of differences between an average value of gray scale values measured from the partial images and the gray scale values is larger than a predetermined reference value.

5. The apparatus for detecting defects in a wafer according to any one of claims 2 to 4, wherein the optical part comprises:
   a first fly-eye lens comprised of a plurality of fine lens cells having a rectangular cross-section and disposed in a matrix manner, and dividing infrared light emitted from the infrared lamp into a unit of the fine lens cell to output the divided light;
   a second fly-eye lens for converting the divided light into parallel light and outputting the parallel light; and
   a collecting lens for collecting the infrared light transmitted through the second fly-eye lens onto the wafer.

6. The apparatus for detecting defects in a wafer according to claim 5, wherein the optical part further comprises a cold mirror for reflecting visible wavelengths of the infrared light emitted from the infrared lamp and transmitting infrared wavelengths.

7. The apparatus for detecting defects in a wafer according to any one of claims 2 to 4, wherein the defect detection part comprises:

an inspection image generating part for combining the image signals to generate an inspection image corresponding to the wafer to be inspected; and a defect determination part for determining a region composed of pixels in which an absolute value of a difference between gray scale values of pixels constituting the generated inspection image and a pre-set reference gray scale value is larger than a predetermined reference value as a defect region, and outputting the position and size of the defect region.

8. The apparatus for detecting defects in a wafer according to claim 7, wherein the defect determination part detects a defect region having a diameter larger than a predetermined reference diameter among the defect regions as a defect existing in the wafer.

9. The apparatus for detecting defects in a wafer according to claim 1, wherein the optical part comprises:
   a first fly-eye lens comprised of a plurality of fine lens cells having a rectangular cross-section and disposed in a matrix manner, and dividing the infrared light into a unit of the fine lens cell to output the divided light;
   a second fly-eye lens for converting the divided light into parallel light and outputting the parallel light; and
   a collecting lens for collecting the infrared light transmitted through the second fly-eye lens onto the wafer.

10. The apparatus for detecting defects in a wafer according to claim 9, wherein the optical part further comprises a cold mirror for reflecting visible wavelengths of the infrared light emitted from the infrared lamp and transmitting infrared wavelengths.

11. The apparatus for detecting defects in a wafer according to claim 1, wherein the optical part comprises:
    an infrared lamp for emitting infrared light;
    an optical transmission path for transmitting the infrared light emitted from the infrared lamp; and
    a linear light guide for converting the infrared light transmitted through the optical transmission path into linear light.

12. The apparatus for detecting defects in a wafer according to claim 9 or 11, wherein the defect detection part comprises:
    an inspection image generating part for combining the image signals to generate an inspection image corresponding to the wafer to be inspected; and
    a defect determination part for determining a region composed of pixels in which an absolute value of a difference between gray scale values of pixels constituting the generated inspection image and a pre-set reference gray scale value is larger than a predetermined reference value as a defect region, and outputting the position and size of the defect region.

13. The apparatus for detecting defects in a wafer according to claim 12, wherein the defect determination part detects a defect region having a diameter larger than a predetermined reference diameter among the defect regions as a defect existing in the wafer.

14. The apparatus for detecting defects in a wafer according to any one of claims 1, 2, 9 and 11, further comprising:
    a wafer conveying part for extracting the wafer from a supply cassette, in which wafers are mounted, to convey the wafer to the inspection region, and removing the wafer from the inspection region when defect inspection by the defect detection part is completed;
    a first cassette for accommodating the wafer having defects therein among the wafers; and
    a second cassette for accommodating the wafer having no defect among the wafers.

15. The apparatus for detecting defects in a wafer according to claim 14, further comprising an alignment part for recognizing a flat zone formed at the wafer to align the wafer,
  wherein the wafer conveying part conveys the wafer to the alignment part to align the wafer, and then conveys the wafer to the inspection region.

16. The apparatus for detecting defects in a wafer according to claim 14, further comprising:
  an optical character reading part for reading inherent identification information given to the wafer, from the wafer; and
  a detection result storage part for storing the defect detection result by the defect detection part on the basis of the identification information read from the wafer.

17. The apparatus for detecting defects in a wafer according to claim 14, further comprising:
  a second inspection stage having an inspection region, on which a wafer is disposed, formed of a transmissive material;
  a second wafer conveying part for extracting the wafer accommodated in the first cassette to convey the wafer onto the inspection region of the second inspection stage, and removing the wafer disposed on the inspection region of the second inspection stage when the defect inspection is completed;
  a second optical part disposed under the second inspection stage and radiating infrared light onto the wafer disposed on the second inspection stage;
  an area camera for outputting an second image signal obtained by detecting infrared light transmitted through the wafer disposed on the second inspection stage;
  a camera drive part for moving the area camera such that a focus of the area camera is formed at a position of the defect existing in the wafer disposed on the second inspection stage, being driven from one surface of the wafer disposed on the second inspection stage to the other surface thereof in a direction perpendicular to the surface of the wafer, and outputting a pulse signal having a predetermined period corresponding to a straight moving distance of the area camera;
  a camera controller for counting the pulse signal input from the camera drive part, and outputting a photographing instruction signal controlling the area camera to photograph the wafer disposed on the second inspection stage whenever a pre-set number of pulse signals is input; and
  a defect depth detection part for detecting a depth of the defect existing in the wafer disposed on the second inspection stage on the basis of the counted number of accumulated pulse signals at the time when a photographing instruction signal corresponding to an image signal having a clearest defect region among the second image signals photographed by the area camera according to the photographing instruction signal is output.

18. The apparatus for detecting defects in a wafer according to any one of claims 1, 2, 9 and 11, further comprising:
  a second inspection stage having an inspection region, on which a wafer having the defect position detected by the defect detection part is disposed, formed of a transmissive material;
  a second optical part disposed under the second inspection stage and radiating infrared light onto the wafer disposed on the second inspection stage;
  an area camera for outputting an second image signal obtained by detecting infrared light transmitted through the wafer disposed on the second inspection stage;
  a camera drive part for moving the area camera such that a focus of the area camera is formed at a position of the defect existing in the wafer disposed on the second inspection stage, being driven from one surface of the wafer disposed on the second inspection stage to the other surface thereof in a direction perpendicular to the surface of the wafer, and outputting a pulse signal having a predetermined period corresponding to a straight moving distance of the area camera;
  a camera controller for counting a pulse signal input from the camera drive part, and outputting a photographing instruction signal controlling the area camera to photograph the wafer disposed on the second inspection stage whenever a pre-set number of pulse signals is input; and
  a defect depth detection part for detecting a depth of the defect existing in the wafer disposed on the second inspection stage on the basis of the counted number of accumulated pulse signals at the time when a photographing instruction signal corresponding to an image signal having a clearest defect region among the second image signals photographed by the area camera according to the photographing instruction signal is output.

19. The apparatus for detecting defects in a wafer according to claim 18, wherein the defect detection part comprises:
  an inspection image generating part for combining the image signals to generate an inspection image corresponding to the wafer; and
  a defect determination part for determining a region composed of pixels in which an absolute value of a difference between gray scale values of pixels constituting the generated inspection image and a pre-set reference gray scale value is larger than a predetermined reference value as a defect region, and outputting the position and size of the defect region.

20. The apparatus for detecting defects in a wafer according to any one of claims 1, 2, 9 and 11, wherein the infrared light radiated from the optical part has a wavelength of 750 nm-850 nm.

21. The apparatus for detecting defects in a wafer according to any one of claims 1, 2, 9 and 11, wherein the defect is an air-pocket existing in the wafer.

22. A method of detecting defects in a wafer, comprising:
  (a) positioning a wafer to be inspected in an inspection region on an inspection stage, the inspection region being formed of a transmissive material;
  (b) conveying an image obtaining apparatus having a plurality of line sensors having a striped photographing region respectively, or the inspection stage in a short-side direction of a photographing region of the line sensor, and outputting a pulse signal having a predetermined period corresponding to a relative straight moving distance between the image obtaining apparatus and the inspection stage;
  (c) counting the pulse signal and outputting a photographing instruction signal to the image obtaining apparatus whenever the wafer is conveyed in the short-side direction of the photographing region of the line sensor toward the image obtaining apparatus by a distance corresponding to the length of short sides of the photographing region;
  (d) detecting infrared light radiated from a light source disposed under the inspection stage and transmitted through the wafer using the image obtaining apparatus, and outputting an image signal; and
  (e) combining the image signals to generate an inspection image corresponding to the wafer, and detecting positions of defects existing in the wafer from the generated inspection image,
  wherein each of the line sensors transmits charges accumulated therein to a line sensor adjacent in an opposite direction of the conveyance direction when a photographing instruction signal is input, and then detects the infrared light transmitted through the wafer disposed on the inspection stage, and the line sensor positioned at an end in an opposite direction of the conveyance direction outputs charges accumulated therein as the image signal from a time when the number of input photographing signals exceeds the number of line sensors.

23. The method of detecting defects in a wafer according to claim 22, further comprising:
   (f) detecting a plurality of partial images for adjusting optical uniformity from an inspection image of a sample wafer having no defect, and
   (g) driving a positioning stage movable in three axial directions constituting an orthogonal coordinate system to change a position of the light source when a difference between the highest and the lowest of gray scale values measured from the partial images exceeds a predetermined reference value.

24. The method of detecting defects in a wafer according to claim 22, further comprising:
   (f) detecting a plurality of partial images for adjusting optical uniformity from an inspection image of a sample wafer having no defect, and
   (g) driving a positioning stage movable in three axial directions constituting an orthogonal coordinate system to change a position of the light source when the highest of differences between an average value of gray scale values measured from the partial images and the gray scale values exceeds a predetermined reference value.

25. The method of detecting defects in a wafer according to any one of claims 22 to 24, wherein step (e) comprises:
   (e1) combining the image signals to generate an inspection image corresponding to the wafer; and
   (e2) determining a region composed of pixels in which an absolute value of a difference between gray scale values of pixels constituting the generated inspection image and a pre-set reference gray scale value is larger than a predetermined reference value as a defect region, and outputting the position and size of the defect region.

26. The method of detecting defects in a wafer according to claim 25, wherein, in step (e2), a defect region having a diameter larger than a predetermined reference diameter among the defect regions is detected as a defect existing in the wafer.

27. The method of detecting defects in a wafer according to claim 22, further comprising:
   (f) accommodating the wafer having defects therein among the wafers into a first cassette; and
   (g) accommodating the wafer having no defect among the wafers into a second cassette.

28. The method of detecting defects in a wafer according to claim 22 or 27, further comprising: before step (a)
   (a1) recognizing a flat zone formed at the wafer to align the wafer; and
   (a2) conveying the aligned wafer to the inspection region.

29. The method of detecting defects in a wafer according to claim 22 or 27, further comprising:
   reading, inherent identification information given to the wafer, from the wafer before step (a); and
   storing the defect detection result of the wafer on the basis of the identification information read from the wafer after step (e).

30. The method of detecting defects in a wafer according to claim 27, further comprising:
   (h) extracting a wafer accommodated in the first cassette to convey the wafer onto an inspection region formed of a transmissive material on a second inspection stage;
   (i) moving an area camera such that a focus of the area camera is formed at a position of the defect existing in the wafer disposed on the second inspection stage, driving the area camera from one surface of the wafer disposed on the second inspection stage to the other surface thereof in a direction perpendicular to the surface of the wafer, and outputting a pulse signal having a predetermined period corresponding to a straight moving distance of the area camera;
   (j) counting the pulse signal, and detecting infrared light radiated from a second light source disposed under the second inspection stage and transmitted through the wafer disposed on the second inspection stage using the area camera whenever a pre-set number of pulse signals is input to obtain an second image signal; and
   (k) detecting a depth of the defect existing in the wafer disposed on the second inspection stage on the basis of the counted number of accumulated pulse signals at the time when a photographing instruction signal corresponding to an image signal having a clearest defect region among the second image signals photographed by the area camera is output.

31. The method of detecting defects in a wafer according to claim 22, further comprising:
   (f) conveying the wafer, a defect position of which is recognized, onto an inspection region formed of a transmissive material on a second inspection stage;
   (g) moving an area camera such that a focus of the area camera is formed at a position of the defect existing in the wafer disposed on the second inspection stage, driving the area camera from one surface of the wafer disposed on the second inspection stage to the other surface thereof in a direction perpendicular to the surface of the wafer, and outputting a pulse signal having a predetermined period corresponding to a straight moving distance of the area camera;
   (h) counting the pulse signal, and detecting infrared light radiated from a second light source disposed under the second inspection stage and transmitted through the wafer disposed on the second inspection stage using the area camera whenever a pre-set number of pulse signals is input to obtain an second image signal; and
   (i) detecting a depth of the defect existing in the wafer disposed on the second inspection stage on the basis of the counted number of accumulated pulse signals at the time when a photographing instruction signal corresponding to an image signal having a clearest defect region among the second image signals photographed by the area camera is output.

32. The method of detecting defects in a wafer according to claim 31, wherein step (e) comprises:
   (e1) combining the image signals to generate an inspection image corresponding to the wafer; and
   (e2) determining a region composed of pixels in which an absolute value of a difference between gray scale values of pixels constituting the generated inspection image and a pre-set reference gray scale value is larger than a predetermined reference value as a defect region, and outputting the position and size of the defect region.

33. The method of detecting defects in a wafer according to any one of claims 22, 27, 30, 21 and 32, wherein the infrared light radiated from the light source has a wavelength of 750 nm-850 nm.

* * * * *